United States Patent [19]

Irie

[11] Patent Number: 5,370,657
[45] Date of Patent: Dec. 6, 1994

[54] RECOVERABLE THROMBOSIS FILTER

[75] Inventor: Toshiyuki Irie, Tokorozawa, Japan

[73] Assignee: Scimed Life Systems, Inc., Maple Grove, Minn.

[21] Appl. No.: 42,424

[22] Filed: Mar. 26, 1993

[51] Int. Cl.⁵ ............................................ A61M 29/00
[52] U.S. Cl. ................................................... 606/200
[58] Field of Search .............................. 606/152–155, 606/191, 108, 198, 200; 128/898, 899; 604/104, 105

[56] References Cited

U.S. PATENT DOCUMENTS

| | | |
|---|---|---|
| 3,334,629 | 8/1967 | Cohn . |
| 3,467,102 | 9/1969 | Fogarty et al. . |
| 3,540,431 | 11/1970 | Mobin-Uddin . |
| 3,868,956 | 3/1975 | Alfidi . |
| 3,952,747 | 4/1976 | Kimmell . |
| 4,425,908 | 7/1984 | Simon . |
| 4,430,081 | 2/1984 | Timmermans . |
| 4,494,531 | 1/1985 | Gianturco . |
| 4,619,246 | 10/1986 | Molgaard-Nielsen . |
| 4,643,184 | 2/1987 | Mobin-Uddin . |
| 4,688,553 | 8/1987 | Metals . |
| 4,727,873 | 3/1988 | Mobin-Uddin . |
| 4,781,177 | 11/1988 | Lebigot . |
| 4,817,600 | 4/1989 | Herms et al. . |
| 4,832,055 | 5/1989 | Palestrant . |
| 4,969,891 | 11/1990 | Gewertz . |
| 4,990,156 | 2/1991 | Lefebvre . |
| 4,998,539 | 3/1991 | Delsanti . |
| 5,035,706 | 7/1991 | Giantureo . |
| 5,059,205 | 10/1991 | El-Nounou et al. . |
| 5,071,407 | 12/1991 | Termin . |
| 5,108,418 | 4/1992 | Lefebvre . |
| 5,108,419 | 4/1992 | Reger et al. . |
| 5,133,733 | 7/1992 | Rasmussen et al. . |
| 5,147,379 | 9/1992 | Sabbaghian et al. . |
| 5,152,777 | 10/1992 | Goldberg et al. . |
| 5,160,342 | 11/1992 | Reger et al. . |
| 5,234,458 | 8/1993 | Metais . |
| 5,242,462 | 9/1993 | El-Nounou et al. . |
| 5,282,824 | 2/1994 | Gianturco ............................ 606/191 |

FOREIGN PATENT DOCUMENTS

| | | |
|---|---|---|
| 117940A2 | 9/1984 | European Pat. Off. . |
| 472334A1 | 2/1992 | European Pat. Off. . |
| 2570288 | 3/1986 | France . |
| 2573646 | 5/1986 | France . |
| 2580504 | 10/1986 | France . |

OTHER PUBLICATIONS

C. J. Grassi, "Inferior Vena Cava Filters: Analysis of Five Currently Available Devices," pp. 813–821, 1991, *AJR*, 156.

G. S. Dorfman, "Percutaneous Inferior Vena Cava Filters." pp. 987–992, 1990, *Radiology*, 174.

R. W. Gunther, H. Schild, A. Fries, and S. Storkel, "Vena Cava Filter to Prevent Pulmonary Embolism: Experimental Study." pp. 315–320, 1985, *Radiology*, 156.

G. Lund, J. Rysavy, E. Salomonowitz et al, "A New Vena Caval Filter for Percutaneous Placement and Retrieval: Experimental Study." pp. 369–372, 1984 *Radiology*, 152.

(List continued on next page.)

*Primary Examiner*—Stephen C. Pellegrino
*Assistant Examiner*—William Lewis
*Attorney, Agent, or Firm*—Willian Brinks Hofer Gilson & Lione

[57] ABSTRACT

A thrombosis filter that has an improved filtering function and can be securely anchored at a desired location and be removed through an endovenous route even after the growth of neointima. The thrombosis filter of this invention includes a first and a second filtering and holding unit, each unit including a coupling mechanism at its outer extremity in the form of a hook, and a plurality of resilient struts which include vein wall junction portions that lie parallel to the vein wall and are biased into contact therewith. The preferred embodiment includes picks that impale the vein wall to a limited depth. The units are interconnected by a core shaft which consists of a compression member and a pair of core wires.

24 Claims, 2 Drawing Sheets

OTHER PUBLICATIONS

J. J. Alexander, B. L. Gewertz, Chien-Tai Lu and C. K. Zarins, "New Criteria for Placement of a Prophylactic Vena Cava Filter." pp. 405–409, 1986 *Surgery Gynecology & Obstetrics*, 163.

P. J. Golueke, W. V. Garrett, J. E. Thompson et al, "Interruption of the Vena Cava by means of the Greenfield filter: Expanding the indications", pp. 111–117, 1988, *Surgery*, 103.

M. D. Darcy, T. P. Smith, D. W. Hunter et al, "Short-term Prophylaxis of Pulmonary Embolism by Using a Retrievable Vena Cava Filter.", pp. 836–838, 1986, *AJR*, 147.

M. H. Awh, F. C. Taylor and Chien-Tai Lu, "Spontaneous Fracture of a Vena-Tech Inferior Vena Caval Filter.", pp. 177–178, 1991, *AJR*, 157.

D. Kim, D. H. Porter, J. B. Siegel & M. Siman, "Perforation of the Inferior Vena Cava with Aortic and Vertebral Penetration by a Suprarenal Greenfield Filter.", pp. 721–723, 1989, *Radiology*, 172.

T. Irie, S. Furui, T. Yamauchi, K. Makita, S. Sawada, E. Takenaka, "Relocatable Gianturco Expandable Metallic Stents.", pp. 575–577, 1991, *Radiology*, 178.

A. M. Palestrant, P. Martin, M. Simon, "Comparative In Vitro Evaluation of the Nitinol Inferior Vena Cava Filter.", pp. 351–355, 1982, *Radiology*, 145.

M. Simon, A. M. Palestrant, "Trasnvenous Devices for the Management of Pulmonary Embolism.", pp. 308–318, 1980, CardioVascular and Interventional Radiology, 3.

G. Lund, J. Rysavy, D. W. Hunter, W. R. Castaneda-Zuniga, K. Amplatz, "Retrievable Vena Caval Filter Percutaneously Introduced.", p. 831, 1985, *Radiology*, 155.

S. Cragg, G. Lund, E. Salomonowitz, J. Rysavy, F. Castaneda, W. Castaneda-Zuniga, K. Amplatz, "A New Percutaneous Vena Cava Filter.", pp. 601–604, 1983, *AJR*, 141.

A. M. Fadali, S. R. Topaz, M. M. Ameli, V. I. Gott, "A filtering device for the prevention of particulate embolization during the course of cardiac surgery.", pp. 634–639, 1968, *SURGERY*, 64.

Castaneda-Zuniga et al, "Seminars in Interventional Radiology." pp. 175–241, 1986, *Thieme Medical Publishers, Inc.*, 3.

M. J. Wallace, K. Ogawa, K. Wright, C. H. Carrasco, W. Richi, C. Charnsangavej, "Inferior Vena Caval Stent Filter.", pp. 148–1250, 1986, *AJR*, 147.

RECOVERABLE THROMBOSIS FILTER

BACKGROUND OF THE INVENTION

The present invention relates to thrombosis filters for trapping blood clots. To be more specific, it relates to thrombosis filters which can be securely fixed at a selected location in the vascular system, and removed when it is no longer required.

In recent years, pulmonary embolism has become an increasingly common medical emergency. Pulmonary embolisms may be caused by venous thrombosis that in turn may be caused by blood flow retention, venous intima damage or coagulation abnormalities. Emergency or prophylactic treatments for these conditions include anticoagulant therapy, thrombolytic therapy, thrombectomy and inferior vena cava blocking procedures.

Among these therapeutic options, when an inferior vena cava blocking procedure is selected, one option is to perform a laparotomy under general anesthesia during which the inferior vena cava is ligated, sutured and shortened, or clipped. A laparotomy however, requires a general anesthetic and is susceptible to thrombosis formation due to the discontinuation of anticoagulant therapy prior to surgery. Another option is to intravenously insert a thrombosis filter into the inferior vena cava which requires a local anesthetic. Percutaneous filter insertion is now more widely employed since it requires only a local anesthetic. However, such filters become fixed in the inferior vena cava wall by neointimal hyperplasia within two or three weeks after being implanted after which they cannot be removed percutaneously.

Blood is returned to the heart from the lower part of the human body through the inferior vena cava and from the upper part of the body through the superior vena cava. The neck vein, known as the jugular vein, leads to the superior vena cava which is a vein that enters the upper part of the heart. A percutaneously inserted catheter that extends through the jugular vein, the superior vena cava and then into the heart can be manipulated to exit the heart through the mouth of the inferior vena cava that opens into the heart. The inferior vena cava, a vein that enters the lower part of the heart, can be accessed through the patients femoral vein. Thus, the inferior vena cava can be reached through two endovenous routes, both of which are available percutaneously.

Figures 1, 2, 3:
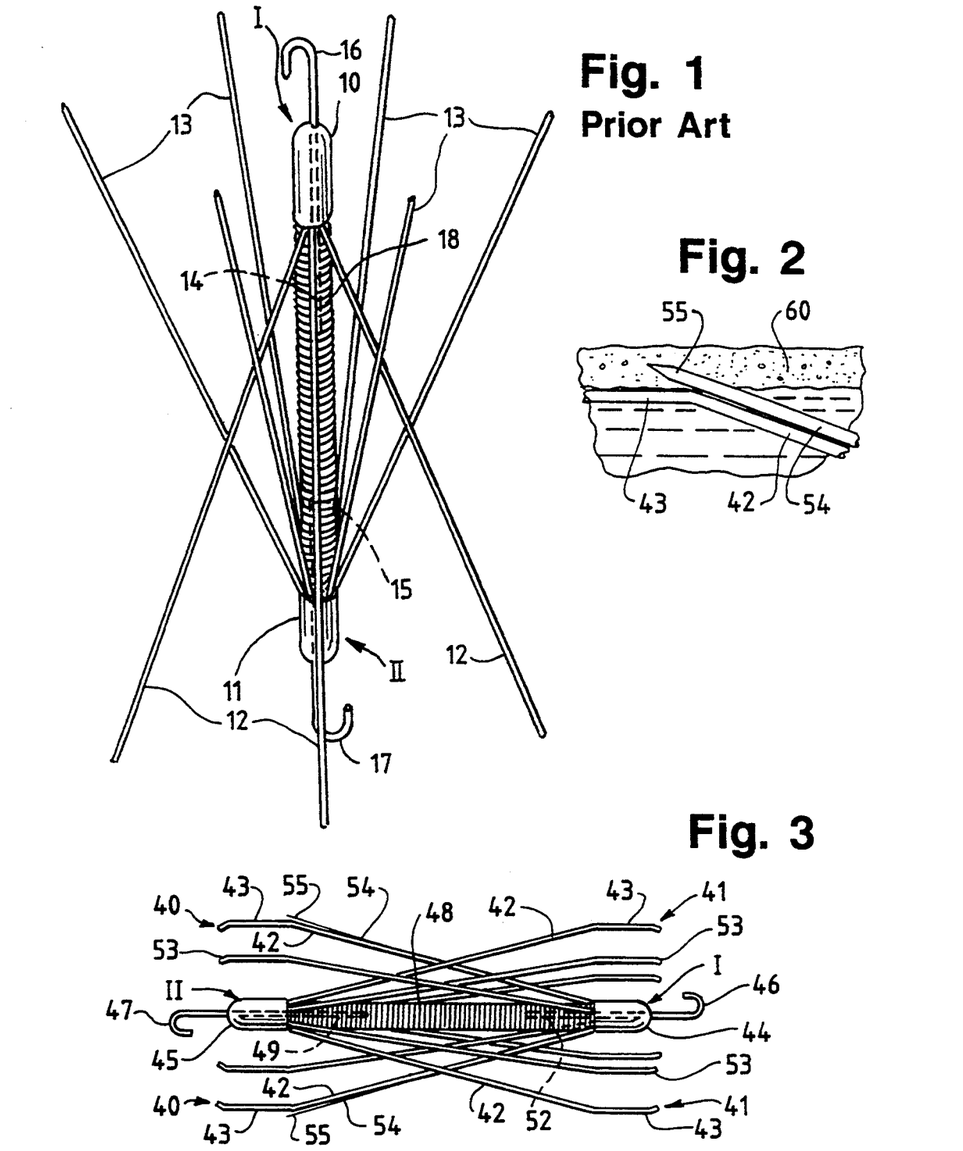
FIG. 1 is a perspective view of a prior art thrombosis filter.
FIG. 2 is a perspective view of the preferred embodiment of the thrombosis filter of this invention.
FIG. 3 is an enlarged view of a portion of the an anchoring unit of FIG. 2 that is impinged in the wall of a blood vessel.

A prior Thrombosis Filter is shown in FIG. 1. A filter of the type shown in FIG. 1, is the subject of PCT application No. PCT/US92/11311. The Thrombosis Filter disclosed in that PCT application can be inserted in the patient and be removed when no longer required requiring only a local anesthetic. The structure of the filter illustrated in FIG. 1 is such that the ends of the struts contact the vein wall at an acute angle and could under some conditions penetrate the wall of the vein in which it has been inserted. If a penetration of this type does occur, in addition to the trauma of a punctured blood vessel, the position of the filter within the blood vessel shifts to a less than optimum position, the likelihood of additional penetrations by other struts increases and removal of the filter becomes more difficult.

SUMMARY OF THE INVENTION

The subject invention fulfills the need of a medical filter which can be positively located and retained at a selected area of a vein with minimum damage to the vein wall and non-surgically removed even after neointima has developed.

The filter includes a first and a second unit, each unit including a plurality of outwardly radiating struts. The units are connected together and extend along a longitudinal axis. The struts of one unit, the heart side unit, form a filtering basket that is blood permeable. The convex side of the filtering basket faces the heart and the concave side opens away from the heart such that blood flowing through the vena cava inferior flows into the concave side of the filtering basket. The basket shaped portion of the other unit, the anchoring unit, opens toward the heart and the blood flow is toward its convex side. Each unit includes a coupling mechanism in the form of a hook which is used in the removal procedure. Each strut includes an initial portion that extends at an acute angle to the longitudinal axis of the filter and a vein wall junction portion that is biased into contact with the vein wall and functions to anchor the filter in place within the vein. The units are interconnected by a core shaft which includes a compression member and a pair of core wires. The compression member can be fractured in response to a tension force of a predetermined quality to divide the filter into separate units that are removed independently.

In the preferred embodiment, each strut has a free end portion that extend back toward the longitudinal axis of the filter to avoid penetration of the vessel wall by the free ends of the vein wall junction portions. Also, picks are provided that extend from the hub in the same direction as the initial portion of the struts and continue a short distance past the intersection between the initial and the vein wall junction portions of the strut.

DETAILED DESCRIPTION OF THE PREFERRED EMBODIMENT

FIG. 1 is a perspective view, of the filtering and holding device that is the subject matter of the above identified PCT Application No. PCT/US92/11311. The invention disclosed in this application is based upon and is an improvement upon the filtering and holding device disclosed in PCT/US92/11311.

The filter device shown in FIG. 1 includes two units I and II that are connected by a compression member in the form of a coil spring 18. As for the structure of the filter units facing each other, this arrangement serves to stabilize and anchor the filter inside the blood vessel and to permit independent movement of one unit relative to the other which benefits the removal procedure. This filter device is unique in that it can be removed through an endovenous route that is available percutaneously, and requiring only a local anesthetic. The struts 12 and 13 that radiate from the central hubs 10 and 11 respectively, of the filter shown in FIG. 1, are straight and their free ends engage the inner surface of the patients vein. Although the struts 12 and 13 engage the vein wall at a shallow angle, under some conditions one or more struts could penetrate the patients vein wall. This filter is fabricated mainly from stainless steel wires. The wire is 0.05 to 0.50 millimeters in diameter. The struts 12 and 13 of the units I and II radiate from the central hubs 10 and 11 respectively in conical configurations and are arranged such that their concave sides face each other. The anchor ends of core wires 14 and 15 are connected to the central hub or fixation parts 10 and 11 along with the straight ends of hooks 16 and 17. The core wires 14 and 15 extend through the lumen formed by coil spring 18 and function as a part of the core shaft to reinforce the coil spring 18 in bending. The core wires 14 and 15 are firmly anchored in the central hubs 24 and 25. When the coil spring is initially bent, the core wires 14 and 15 have no effect on bending, only the resistance to bending of the coil spring must be overcome. When the bending angle is such that the core wires 14 and 15 engage the inner surface of the coil spring, then further bending must also overcome the bending resistance of the core wires, The unanchored ends of core wires 14 and 15 are free. The core wires within the compression member function to improve the bending quality of the core shaft as well as to achieve a desired flexibility for the compression member.

The coupling mechanism, in the form of a hook element provided at the head of each filter unit, functions to connect the unit to mechanism that can be manipulated through an endovenous route at the time of removal. Hooks 16 and 17 are used in the removal procedure and are constructed of tungsten or stainless steel wires that have been bent into the shape shown in FIG. 1.

It should be noted that each of the units illustrated in FIG. 1 have six (6) struts, and all six of the struts from Unit II are shown in the illustration. Since the six struts are equally spaced around the unit, in Unit I some of the six struts are hidden behind foreground struts.

Referring now to FIG. 2 the preferred embodiment of the invention will be described. The filter of this invention includes a filter basket that is permeable to the blood flow but which will catch emboli and thrombus that are being carried in the blood stream and also hold the filter firmly in a selected location and permit removal through an endovenous route. The filtering and holding device of this medical filter includes two units that face each other and are biased toward each other. The units are formed of resilient struts that have initial and vein wall junction portions.

Although the present thrombosis filters can be made from a number of materials the material must be a flexible and must return to its original shape after being deformed such as identity elastic alloy wire, high elastic alloy wire such as stainless steel, tungsten, platinum, piano wire, shape memory alloy wire, super elastic metal wire and chromium alloy. It is important that the coupling mechanisms be constructed of or include material such a tungsten, platinum or gold that can be seen on a fluoroscope, to aid in the process of attaching the coupling mechanisms.

Each unit of the filter includes multiple struts that are anchored in the corresponding central hub and extend therefrom at regular spaced intervals. The initial portions of the struts of each unit lie on the surface of a cone or basket with an anchoring portion of the struts at the apex of the cone. The anchoring portions of the struts are connected to and are a part of the central hub, The thickness of the wire from which the struts are formed is preferably 0.05 to 0.50 millimeters in diameter.

The two units are connected by a core shaft that is flexible, expandable and facilitates maneuvering the filter units into the recovery sheath or sheathes for removal. The core shaft includes a compression member that allows relative movement of the units along the filter's longitudinal axis. The compression member can be designed to fracture when exposed to a predetermined tension force, can be provided with a weakened area that will fracture in response to a tension force of a predetermined amount or can be anchored to the unit hub such that it will be uprooted in response to a tension force of a predetermined amount. The ideal outside diameter of the compression member is in the range of 0.5 to 2 millimeters. Inside the compression member a core wires extends from each of the filter units and function to reinforce the compression member in bending.

The overall size of the thrombosis filters, will be determined by the site of its application and the size of the particular vein into which it will be implanted.

In this embodiment the free end sections are contoured to avoid penetration of the vessel wall and picks are provided that are implanted into the surface of the vessel wall to thereby positively anchor the filter in a desired location. The depth to which the picks can be implanted is limited and thus the trauma and disadvantages associated with uncontrolled penetration of the vessel wall has been eliminated. The picks enter the vein wall at an angle to the filter's longitudinal axis and in the direction such that the fluid flow exerts a constant pressure to force the picks deeper into the vein wall. Thus blood flow through the vein exerts a force on the filter maintaining the limited penetration of the picks in the vein wall.

In the preferred embodiment there are fewer struts in the anchoring unit than in the heart side unit and there are fewer picks in the anchoring unit than struts. In the specific embodiment disclosed herein the heart side unit has six struts and the anchoring unit has four struts and two picks. The length of the picks available for implanting into the vein wall is relatively short, being about equal to the thickness of the vein wall. Since the picks are inserted into the vein wall at an angle, provided their length is equal to the thickness of the vein wall, they will not extend completely through the vein wall. However, the picks effectively serve their purpose of providing the filter with means for positively securing the filter in a preferred location. They serve this purpose while doing minimum damage to the vein wall. When the filter is removed the unit carrying the picks is pulled upstream of the blood flow. Thus, withdrawal of the picks from the vein wall is non-damaging to the vein wall.

The filter device of this embodiment consists of units I and II, that are spaced from each other along the filter's longitudinal axis and which face each other and are connected by a compression member such as a coil spring 48. The term compression member means a member that will draw the filtering and holding units toward each other to thereby minimize the overall longitudinal length of the filter. The compression member could be formed from a flexible, elastic material that has a smooth outer surface. Each unit has a central hub 44, 45 from which a plurality of struts 40, 41 radiate. The struts 40, 41 include initial portions 42 that are anchored in the central hubs 44 and 45 and radiate therefrom at equal angles to the filters longitudinal axis. The struts 40 and 41 also include vein wall junction portions 43 that are bent down toward the filter's longitudinal axis.

It should be understood that some of the struts 40 and 41 could be straight as in the FIG. 1 filter with the result that the straight struts would exert a greater anchoring force and the struts with the vein wall junction portions would stabilize the filter and prevent the straight struts from penetrating the vein wall.

The angles at which the initial portions 42 extend to the longitudinal axis and the downward angle of the vein wall junction portion are dependent upon a number of factors such as the size of the vein in which it will be implanted, the material from which the struts are constructed and the diameter of the strut wire. The unstressed diameter of the filter must be greater than the inside diameter of the vein in which it will be implanted. A filter having an unstressed diameter that is equal to 1.3 times the diameter of the vein into which it is to be implanted has been found to be optimum. When the filter has been implanted in a vein the vein wall junction portions of the strut is parallel to the inner surface of the vein wall and can be biased against it.

In this embodiment, a short sections 53 of the ends of the vein wall junction portions 43 are bent inwardly to thus provide assurance that the free ends of the struts 40 and 41 will not pierce the vein wall.

Unit I of the preferred embodiment, illustrated in FIG. 2, has four struts 40 as compared to the six struts 41 in Unit II. The six struts 41 of Unit II form a filter basket to catch blood clots. Units I and II are connected together by a compression member 48 and there are core wires 52, 49 anchored in the central hubs 44, 45. This embodiment also includes hooks 46, 47 that are used in the removal procedure. Struts 40 are anchored in central hub 44, are equally spaced around hub 44 and radiate therefrom at equal angles.

Unit I of the preferred embodiment, includes a plurality of anchor legs 54 that are securely anchored in central hub 44 and radiate therefrom at the same angle as struts 40. The anchor legs 54 are straight and terminate in pick portions 55. The anchor legs 54 are located such that they are adjacent to corresponding struts 40 and could be secured thereto by welding or adhesive. In the preferred embodiment illustrated in FIG. 2, Unit I has four struts 40 and two anchor legs 54. In this arrangement the anchor legs 54 would be located such that they are diametrically opposite each other. The pick portions 55 of anchor legs 54 extend beyond the intersection of the initial portion 44 and vein wall junction portion 43 of the struts 40. The ends of the pick portions 55 can be sharpened to a point. The length of the pick portion is in the range of 0.50 to 1.00 millimeters, which does not exceed the usual thickness of the vein wall. Since the picks extend into the vein wall at an angle, picks having a length equal to or less than the usual vein wall will not extend through the vein wall.

In FIG. 3 the vein wall is identified as 60. When the filter of the preferred embodiment is being inserted in a vein, and Unit I tends to moves to the left as seen in FIGS. 2 and 3, causing picks 55 to pierce the vein wall at an angle. The vein wall junction portion 43 of strut 40 will however limit the penetration of pick 55. Thus the cooperation between the vein wall junction portions 43 and the picks 55 will positively anchor the filter at the selected location in the vein wall as well as limit the penetration depth of the picks 55. During the removal procedure Unit I will be pulled to the right, as seen in FIG. 3, and the pick 55 will smoothly slide out of the hole that it has made in the vein wall 60 without causing damage to the vein wall.

Figure 4:
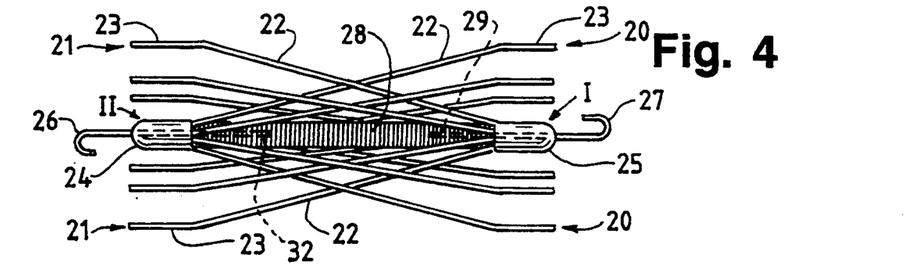
FIG. 4 is a perspective view of another embodiment of the thrombosis filter of this invention.

In FIG. 4 another embodiment of this invention is illustrated that consists of units I and II, that are spaced from each other along the filter's longitudinal axis and which face each other and are connected by a compression member such as a coil spring 28. Each unit has a central hub 24, 25 from which a plurality of struts 20, 21 radiate. The struts 20, 21 include initial portions 22 that are anchored in the central hubs 24 and 25 and radiate therefrom at equal angles to the filters longitudinal axis. The struts 20 and 21 also include vein wall junction portions 23 that are bent down toward the filter's longitudinal axis. The angles at which the initial portions 22 extend to the longitudinal axis and the downward angle of the vein wall junction portion are dependent upon a number of factors such as the size of the vein in which it will be implanted, the material from which the struts are constructed and the diameter of the strut wire. When the filter has been implanted in a vein, the vein wall junction portions of the strut are parallel to the inner surface of the vein wall and are be biased against it.

The filter, illustrated in FIG. 4, is implanted in the vein such that blood flows into the concave shaped basket formed by the struts 21 of Unit I. The struts 21 form a filter basket that is pervious to the flow of blood but will catch and contain blood clots. The initial portions 22 of struts 20 cross the initial portions 22 of struts 21 and thus a portion of struts 20 are within the filtering basket formed by struts 21. The struts are formed from thin resilient wire, for example stainless steel wire, and the angles of the initial portion to the longitudinal axis of the filter and the angle between the initial portion and the vein wall junction portion vary depending upon whether the filter is unconfined, compressed for insertion and removal or in place within a blood vessel.

The struts are resilient and their vein wall junction portions are parallel to and can bear against the inner wall of the vein, when implanted therein. The anchoring of an embodiment of this filter, is accomplished by orientating the two units such that their concave side opens in opposite directions and the entire length of the vein wall junction portion of the struts, of both units, are biased into engagement with the inner wall of the blood vessel. As a result, there is a relatively large friction surface in engagement with the vessel wall that functions to anchor the filter in place. The length of the vein wall junction portions is about 5 millimeters. The pressure exerted by the vein wall junction portions of the struts against the vessel wall is of course determined by the material of the strut, its diameter and the unstressed angles that are built into the filter.

The filter units I and II, of FIG. 4, also include core wires 32, 29, a compression member 28 and hooks 26, 27. The anchor ends of struts 20, 21 are securely anchored in the central hubs 24, 25 such that they radiate at an angle to the filter's longitudinal axis. Core wires 32, 29 are anchored in the units and have free ends that extend from their anchored ends, through compression member 28, toward the other unit. The struts 20, 21 are formed from spring type material and thus can be biased inwardly to decrease the unstressed diameter of the filtering and holding device when it is located in the vein as well as in the insertion and removal tubes. This embodiment relies upon the spring pressure causing the vein wall junction portions to bear against the inner surface of the vein wall to anchor the filter in place. A force must be applied to the filter, sufficient to overcome the friction forces between the twelve vein wall junction portions and the inner surface of the vein wall, in order to move the filter from the location where it was originally implanted.

A welding or binder material is used for brazing the ends of the hooks 26, 27, core wires 32, 29, the struts 20, 21 and the ends of compression member 28 to the central hub or fixation parts 24 and 25. It should be noted that the compression member 28, hooks 26, 27 core wires 32, 29 and the struts 20, 21 can all be fabricated from the same material or each of these parts could be fabricated from different material that will provide the desired characteristics for the particular part.

It is important to measure the inside diameter of the patients inferior vena cava so that the filter that is implanted has an appropriate diameter. If the filter is undersized there is a danger than it could migrate and if it is oversized it is more likely to penetrate the vein wall. A filter having an unstressed diameter equal to 1.3 times the diameter of the vein into which it will be implanted has been found to be optimum. A device has been developed for measuring the inside diameter of the patients inferior vena cava. The device resembles one of the Units of the filter illustrated in FIG. 4 except nine rather than six splaying legs are anchored in the hub. The hub has a longitudinal length of 1 centimeter. The device is inserted into the patients inferior vena cava at the location where the filter will be implanted and a contrast medium is injected. The device is viewed on a scope and the diameter of the inferior vena cava and the length of the hub are measured. Since the scope magnifies, the exact diameter of the inferior vena cava, in centimeters, can be obtained by dividing the measured diameter of the inferior vena cava by the measured diameter of the hub.

Figure 5:
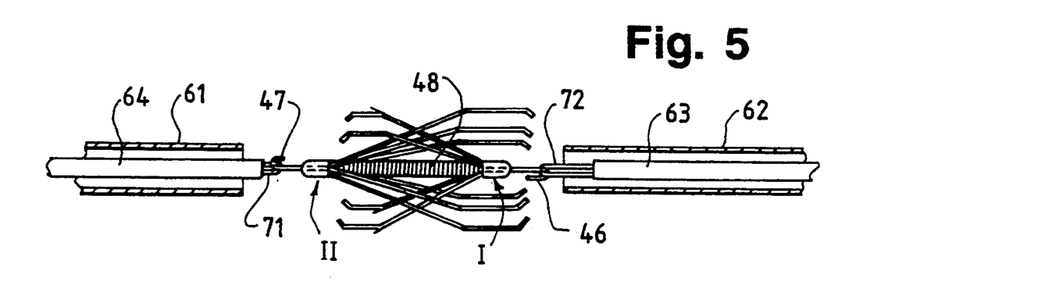
FIG. 5 is a cross-sectional view illustrating a step in the method for removing the thrombosis filter of this invention from a patient.
Figure 6:
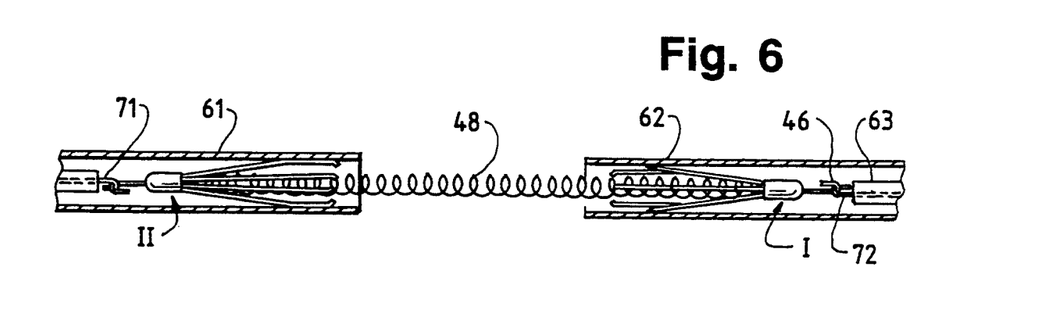
FIG. 6 is a cross-sectional view illustrating a step in the method for removing the thrombosis filter of this invention from a patient.
Figure 7:
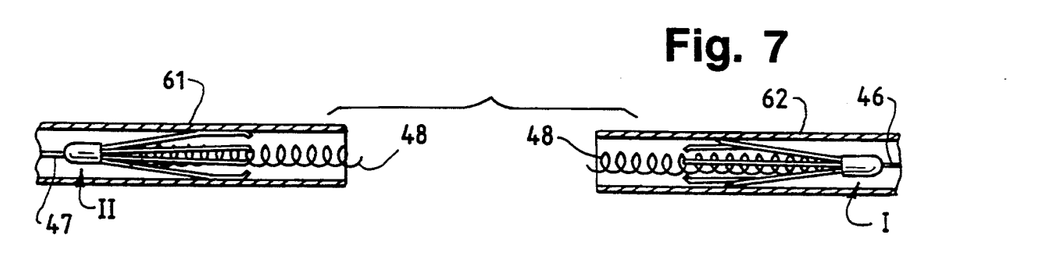
FIG. 7 is a cross-sectional view illustrating a step in the method for removing the thrombosis filter of this invention from a patient.

Referring now to FIGS. 5-7 the method of implanting and removing the thrombosis filter will be discussed and explained. This discussion will be referenced to the preferred embodiment illustrated in FIG. 2 but is should be understood that the discussion applies equally to the embodiment illustrated in FIG. 4. The two units are biased together by a compression member which elongates during the removal procedure until it reaches a point where it fractures thus separating Units I and II of the filter so that the two units can be removed individually.

The thrombosis filter is dimensioned such that it can be stored in the distal end of a thin tube (2 to 3 millimeters inside diameter). This insertion tube is percutaneously inserted into the patient and follows an endovenous route into the patient's inferior vena cava. This procedure is performed under local anesthetic. When the distal end of this tube reaches the target site, the filtering and holding device stored inside the tube is caused to exit the distal end of the tube where it become implanted in the patient's inferior vena cava. A pusher rod is extended through the insertion tube and is maneuverable from the proximate end of the insertion tube for forcing the filtering and holding device out the distal end of the insertion tube. It should be noted that insertion of the filter is monitored on a fluoroscope.

The filtering and holding device after being released from the tube into the patient's inferior vena cava, through the above described procedure, is in the form as shown in FIG. 2. Within several weeks after the filtering and holding device has been implanted in the inferior vena cava, the struts 40 and 41 become covered by neointima.

When it becomes necessary or desirable to remove the filtering and holding device, the following procedure is followed. A recovery device is provided that can be inserted percutaneously and threaded through the endovenous route to the filtering and holding device. The recovery device includes a first tube 64, a second tube or sheath 61, a third tube 63 and a fourth tube or sheath.

Referring to FIG. 5, a doubled over cord 71 is inserted through the proximal end of the first tube 64 such that the cord emerges, in the form of a loop, at the distal end of the tube 64 where in functions as a coupling mechanism. The tube 64 is then passed through the second tube or sheath 61 which has been percutaneously inserted into the patient via the right internal jugular vein, through the superior vena cava and into the inferior vena cava, such that its distal end is adjacent the filtering and holding device. The tube 64 is advanced, through tube or sheath 61, to the filtering and holding device where it is manipulated such that its coupling mechanism is grasped by the complementary hook coupling mechanism 47.

In the same manner, a doubled over cord 72 is passed through third tube 63 such that a loop that functions as a coupling mechanism emerges from the distal end of the tube. Third tube 63 is threaded through a fourth tube or sheath 62 which was percutaneously inserted into the patient via the femoral vein such that its distal end is in the patient's inferior vena cava The third tube 63 is manipulated such that its coupling mechanism is grasped by the complementary hook coupling mechanism 46. Cords 71 and 72 are made of or include radiopaque material such as stainless steel so that the coupling of the loops with hooks 46 and 47 can be monitored on a scope.

Referring now to FIG. 6, after cord 71 is connected to hook 47 and cord 72 is connected to hook 46 the cords 71 and 72 are simultaneously pulled in opposite directions, causing units I and II to move away from each other. The compression member 48 initially expands to permit this relative movement of units I and II. The relative movement of units I and II has resulted in a corresponding movement of the struts 40 and 41 relative to the vessel wall and the filter have been freed from the neointima. This movement has also pulled the picks 55 from their nest in the vessel wall 60.

The next step in the removal procedure of the filtering and holding device is illustrated in FIG. 7. Tension on cords 71 and 72 have been increased to the point where compression member 48 has fractured and Units I and II have separated from each other. Compression member 48 is made from material that can be fractured by manually applying tension in opposite directions to cords 71 and 72. After compression member 48 has fractured the cords 71 and 72 would be pulled sufficiently to insure that the loose ends of compression member 48 are completely confined within sheathes 61 and 62 and then sheaths 61 and 62 are withdrawn from the patient. Sheath 61 is thus removed from the patient along with Unit I and sheath 62 is removed from the patient along with Unit II.

Figure 8:
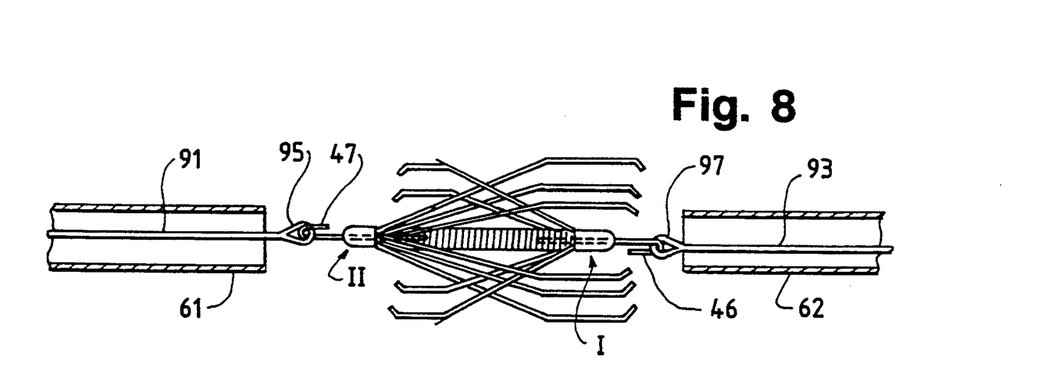
FIG. 8 is a cross-sectional view, similar to FIG. 5 but illustrating another embodiment of tools to be used in the removal procedure.

Referring now to FIG. 8, which is a view similar to FIG. 5, showing the first step in the removal procedure using different removal tools. In FIG. 8, a wire 91 having a loop 95 formed in its distal end is used instead of the cord 71 and first tube 64 that were used in the removal procedure illustrated in FIGS. 5-7. The wire 91 has sufficient stiffness that it can be guided and manipulated from its proximal end to couple loop 95 with hook 47 and also possess the necessary flexibility that it can follow the turns and curves of sheath 61. Wire 91 can be made of wire of the type used in the construction of angioplasty guide wires. In this removal procedure the sheath 61 is percutaneously inserted into the patient via the right internal jugular vein, through the superior vena cava and into the inferior vena cava, such that its distal end is adjacent the filtering and holding device. The wire 91 is threaded, loop 93 first, through sheath 61 from its proximal end. While being viewed on a scope the loop 95 is coupled with the hook 47. In the FIG. 8 removal procedure embodiment, a second wire 93 having a loop 97 formed at its distal end is used instead of the cord 72 and third tube 63 that were used in the removal procedure shown in FIGS. 5-7. Although closed loops 95 and 97 have been disclosed, hook shaped couplers could also be used. Wires 91 and 93 are made of the same material and function in the same way to couple to both ends of the filter's hooks 47 and 46. After the coupling has been made between wires 91 and 93 with hooks 47 and 46 respectively, the same procedure is followed as describes above with reference to FIGS. 6 and 7 for separating Unit I and Unit II. The force on wires 91 and 93 in opposite directions is then increased until the compression member 48 is fractured. Compression member 48 is designed to fracture at a predetermined tension force. At this point of the removal procedure Units I and II are independently stored in sheaths 61 and 62, which can be removed from the patient.

When the filters used for the present invention are employed in blood vessels, in order to prevent the adhesion of thrombosis it is preferable to coat the filters with an antithrombotic agent (such as heparin, urokinase and antithrombotic material including hydroxy methacrylate-styrene copolymer).

During the implanting process an insertion tube, containing the filter, is percutaneously inserted into the patient's inferior vena cava through the femoral vein. The filtering and holding device is expelled from the distal end of the insertion tube, by a pusher rod and is implanted at a selected location in the inferior vena cava. When the filter is expelled from the insertion tube it is propelled, by blood flow, in the direction that will cause the picks 55 to impale the wall of the vein and thus insure that the filter will remain at the selected location.

It is intended that the accompanying Drawings and foregoing detailed description is to be considered in all respects as illustrative and not restrictive, the scope of the invention is intended to embrace any equivalents, alternatives, and/or modifications of elements that fall within the spirit and scope of the invention, and all changes which come within the meaning and range of equivalency of the claims are therefore intended to be embraced therein.

It is claimed:

1. A filter formed along a longitudinal axis, to be placed in the blood vessel of a patient for trapping clots,
    said filter including first and second units that are spaced from each other along the filter's longitudinal axis,
    each of said units including a central hub into which a plurality of struts are anchored such that they radiate outwardly therefrom at an acute angle to said longitudinal axis in the direction toward the other of said units,
    said first and second units being interconnected by an elongated compression member extending along said longitudinal axis, each end of said compression member being connected to the central hub of one of said units,
    the struts of the first unit including initial portions that form a filter basket having a concave side that functions to capture clots that are flowing through the blood vessel toward the concave side of the filter basket, the struts of the first unit are bent toward the longitudinal axis at the ends of their initial portion to form vein wall junction portions that extend parallel to the vein wall and are biased into engagement therewith such that the vein wall junction portions function to anchor the filter at a desired position within the blood vessel,
    the struts of the second unit including initial portions that form a cone, the struts of the second unit are bent toward the longitudinally axis at the ends of their initial portion to form vein wall junction portions that extend parallel to the vein wall.

2. The invention as set forth in claim 1, wherein each unit of said filter includes a core wire, one end of each core wire is anchored in the unit's central hub and extends from its anchor toward the other unit, said core wires terminating in free ends short of said other unit.

3. The invention as set forth in claim 2 wherein said filter includes a coupling mechanism at each of its ends, each of said coupling mechanisms being connected to the central hub of its associated unit and being accessible percutaneously through the blood vessel in which the filter is implanted.

4. The invention as set forth in claim 2 in which the struts of said first and second units are made of spring material and include an anchoring portion that are rigidly anchored in said central hubs, said struts being equally spaced around the central hubs such that engagement by the vein wall junction portions of the struts causes the corresponding central hubs to be located along said longitudinal axis.

5. The invention as set forth in claim 1 wherein said filter includes a coupling mechanism at each of its ends, each of said coupling mechanisms being connected to the central hub of its associated unit and being accessible percutaneously through the blood vessel in which the filter is implanted.

6. The invention as set forth in claim 1 in which the struts of said first and second units are made of spring material and include an anchoring portion that are rigidly anchored in said central hubs, said struts being equally spaced from adjacent struts such that engagement by the vein wall junction portions of the struts causes the corresponding central hub to be located along said longitudinal axis.

7. The invention as set forth in claim 1, wherein said vein wall junction portions of the struts of the first unit are biased into engagement with the vein wall to anchor the filter at a desired position within the blood vessel.

8. A filter formed along a longitudinal axis, to be placed in the blood vessel of a patient for trapping clots, said filter including first and second units that are
- spaced from each other along the filter's longitudinal axis,
- each of said units including a central hub into which a plurality of struts are anchored such that they radiate outwardly therefrom at an acute angle to said longitudinal axis in the direction toward the other of said units,
- said first and second units being interconnected by an elongated compression member extending along said longitudinal axis, each end of said compression member being connected to the central hub of one of said units,
- the struts of the first unit including initial portions that form a filter basket having a concave side that functions to capture clots that are flowing through the blood vessel toward the concave side of the filter basket, the struts of the first unit are bent toward the longitudinally axis at the ends of their initial portion to form vein wall junction portions that extend parallel to the vein wall and are biased into contact therewith such that the vein wall junction portions function to anchor the filter at a desired position within the blood vessel,
- the struts of the second unit including initial portions that form a cone, the struts of the second unit are bent toward the longitudinally axis at the ends of their initial portion to form vein wall junction portions that extend parallel to the vein wall and are biased into engagement therewith such than the vein wall junction portions function to anchor the filter at a desired position within the blood vessel,
- said second unit further including anchor legs that are anchored in said central hub and radiate outwardly therefrom at an acute angle to said longitudinal axis generally parallel to the initial portions for the secondary unit struts, said anchor legs extend past the intersection of the initial and vein wall junction portion of the second unit struts and terminate in picks that can pierce the vein wall at an acute angle thereto.

9. The invention as set forth in claim 8, wherein the struts of the first unit are bent toward the longitudinally axis at the ends of their vein wall junction portion to form inwardly directed end portions that will avoid piercing the vein wall.

10. The invention as set forth in claim 9 wherein said first unit has six struts and the second unit has four struts.

11. The invention as set forth in claim 8, wherein the struts of the second unit are bent toward the longitudinally axis at the ends of their vein wall junction portion to form inwardly directed end portions that will avoid piercing the vein wall.

12. The invention as set forth in claim 11 wherein said first unit has six struts and the second unit has four struts.

13. The invention as set forth in claim 8 wherein said first unit has six struts and the second unit has four struts.

14. The invention as set forth in claim 13 wherein said first unit has six struts and the second unit has four struts.

15. The invention as set forth in claim 13 wherein said anchor legs are each connected to the initial portion of a second unit strut.

16. The invention as set forth in claim 13 wherein that are two anchor legs.

17. The invention as set forth in claim 8 wherein said anchor legs are each connected to the initial portion of a second unit strut.

18. The invention as set forth in claim 8 wherein that are two anchor legs.

19. A method of recovering a filter that has been implanted in the vascular system of a patient, said filter being of the type that extends along the longitudinal axis of a blood vessel and includes first and second units connected by a compression member, said filter includes coupling mechanisms at each of its ends, comprising the steps of:
(a) inserting a first recovery tube into the patient's vascular system that leads to the first end of the implanted filter;
(b) advancing the first recovery tube through the patients vascular system to the point where the distal end of the first recovery tube is in the vicinity of a first end of the implanted filter;
(c) inserting a second recovery tube into the patient's vascular system that leads to a second end of the implanted filter;
(d) advancing the second recovery tube through the patient's vascular system to the point where the distal end of the second recovery tube is in the vicinity of the second end of the implanted filter;
(e) providing a first elongated member having a coupling mechanism, that is complementary to the coupling mechanism on the filter;
(f) advancing the first elongated member through the first recovery tube until the coupling mechanism on the first end of the filter and on the distal end of the first elongated member are adjacent;
(g) manipulating the first elongated member from its proximal end to cause the adjacent coupling mechanism on the first end of the filter and the distal end of the first elongated member to become attached;
(h) provide a second elongated member having a coupling mechanism, is complementary to the coupling mechanisms on the filter; elongated member;
(i) advancing the second elongated member through the second recovery tube until the coupling mechanisms on the second end of the filter and on the distal end of the second elongated member are adjacent;
(j) manipulating the second elongated member from its proximal end to cause the adjacent coupling mechanisms on the second end of the filter and the distal end of the second elongated member to become attached;
(k) applying a pressure in the proximal direction on the first and second elongated members causing said compression member to expand and said first and second filter units to move away from each other and to separate from the vessel;
(l) continue to apply pressure in the proximal direction on the first and second elongated members until said compression member fractures and said first and second filter units are separated; and (m) withdraw the recovery tubes, each containing one of the filter units, from the patient.

20. The method as set forth in claim 19 wherein said elongated members are hollow tubes and said coupling mechanism at the distal ends of said elongated members are formed by:

(1) doubling cords over so that the cords have a loop at one end;

(2) advancing the cord, loop end first, through said hollow tubes toward their distal end, until the loop exits the hollow tubes at the distal end and functions as the coupling mechanism for coupling to said filter.

21. The method as set forth in claim 19 wherein said elongated members are stiff wires having coupling mechanisms at their distal ends.

22. A method of removing a filter that has been implanted in a patients vascular system comprising the steps of:

(a) percutaneously inserting a pair of recovery tubes into vessels of the patient's vascular system that lead to both ends of the filter;

(b) advancing the pair of recovery tubes through the patient's vascular system until their distal ends are adjacent to the filter;

(c) advancing an elongated member having a coupling mechanism on its distal end through each of said recovery tubes until the coupling mechanisms contact the filter;

(d) coupling said coupling mechanisms to the opposite ends of the filter;

(e) exerting a tension force on said elongated members in opposite directions until the filter fractures into two distinct and separate units;

(f) pulling each of the distinct and separate units into the distil end of a recovery tube; and (g) percutaneously withdrawing the recovery tubes, each containing one of the distinct and separate units, from the patient.

23. A method on implanting a filter, of the type that includes first and second units connected by a resilient coupling member and having coupling mechanisms at its first end and at its second end, into a vessel of a patient and recovering the filter when it is no longer needed, comprising the steps of:

(a) measuring the inside diameter of the vessel into which the filter is to be implanted;

(b) selecting a filter that has an unstressed diameter in excess of the inside diameter into which it will be implanted;

(c) implanting percutaneously the selected filter into the patients vessel;

(d) performing the following step to percutaneously remove the filter when it is no longer needed by the patient;

(e) inserting a first recovery tube into the patient's vessel that leads to the implanted filter;

(b) advancing the first recovery tube through the patients vascular system to the point where the distal end of the first recovery tube is in the vicinity of the first end of the implanted filter;

(c) inserting a second recovery tube into the patient's vessel that leads to the second end of the implanted filter;

(d) advancing the second recovery tube through the patients vascular system to the point where the distal end of the second recovery tube is in the vicinity of the second end of the implanted filter;

(e) provide a coupling mechanism, that is complementary to the coupling mechanisms on the filter, on the distal end of a first elongated member;

(f) advancing the first elongated member through the first recovery tube until the complementary coupling mechanisms on the first end of the filter and on the distal end of the first elongated member are adjacent;

(g) manipulating the first elongated member from its proximal end to cause the adjacent coupling mechanism on the first end of the filter and the distal end of the first elongated member to become attached;

(h) provide a coupling mechanism, that is complementary to the coupling mechanisms on the filter, on the distil end of a second elongated member;

(f) advancing the second elongated member through the second recovery tube until the complementary coupling mechanisms on the second end of the filter and on the distal end of the second elongated member are adjacent;

(g) manipulating the second elongated member from its proximal end to cause the adjacent coupling mechanisms on the second end of the filter and the distal end of the second elongated member to become attached;

(k) applying pressure in the proximal directions on the first and second elongated members causing said compression member to expand and said first and second filter units to move away from each other and separate from the vessel;

(l) continuing to apply pressure in the proximal directions on the first and second elongated members until said compression member fractures and said first and second filter units are separated from each other and are pulled into the distal ends of the first and second recovery tubes; and (m) withdrawing the recovery tubes, each containing one of the filter units, from the patient.

24. The invention as set forth in claim 23 wherein the selected filter has an unstressed diameter equal to about 1.3 times the inside diameter of the vessel into which it will be implanted.

* * * * *